United States Patent [19]

Diamond

[11] 4,089,959
[45] May 16, 1978

[54] LONG-ACTING XANTHINE BRONCHODILATORS AND ANTIALLERGY AGENTS

[75] Inventor: Julius Diamond, Morris Plains, N.J.

[73] Assignee: Cooper Laboratories, Inc., Parsippany, N.J.

[21] Appl. No.: 672,437

[22] Filed: Mar. 31, 1976

[51] Int. Cl.$^2$ .................... A61K 31/52; C07D 473/06
[52] U.S. Cl. .................................... 424/253; 544/273
[58] Field of Search .................. 260/256; 424/253

[56] References Cited

U.S. PATENT DOCUMENTS

| 2,729,643 | 1/1956 | Stoll et al. | 260/256 |
| 3,624,215 | 11/1971 | Stein et al. | 424/253 |
| 3,624,216 | 11/1971 | Stein et al. | 424/253 |
| 3,632,742 | 1/1972 | Eckert et al. | 260/256 |

OTHER PUBLICATIONS

Armitage et al.; Brit. J. Pharmacol. (1961), 17, 196–207.
Cutting, Handbook of Pharmacology, 4th Edition, pp. 294–296.

Primary Examiner—Leonard Schenkman
Attorney, Agent, or Firm—Thomas R. Boland

[57] ABSTRACT

Prolonged bronchodilation and prolonged inhibition of allergic mediator release in mammals are produced by administering an effective amount of a substituted xanthine compound having the formula:

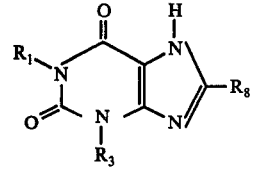

wherein:
$R_1$ = methyl
$R_3$ = $C_4$–$C_7$ alkyl, $C_4$–$C_7$ cycloalkylalkyl $C_4$–$C_7$ alkenyl, $C_4$–$C_7$ alkynyl, or $C_4$–$C_7$ cycloalkyl
$R_8$ = $C_1$–$C_2$ alkyl These compounds are useful in the treatment of bronchial asthma and other bronchospastic and allergic diseases. The compounds are also novel.

The bronchodilator and antiallergy agents may be administered in the form of tablets, capsules, aerosols, solutions, suspensions or suppositories.

34 Claims, No Drawings

LONG-ACTING XANTHINE BRONCHODILATORS AND ANTIALLERGY AGENTS

BACKGROUND OF THE INVENTION

This invention relates to methods for treatment of bronchial asthma and other bronchospastic and allergic diseases. More particularly it relates to a method of treating these diseases employing certain substituted xanthine compounds.

Bronchial asthma is characterized by bronchospasm caused by contraction of the bronchial smooth muscle, increased secretion of mucus from the bronchi, and edema of the respiratory mucosa. While the etiology of asthma is not completely known, it is believed to involve an allergic reaction. Allergic reactions occur in sensitized individuals who are exposed to the antigen to which they are sensitized. The antigen provokes the release in the body of certain chemicals (allergic mediators) which in turn produce the allergic symptoms. Allergic reactions can also produce effects in organs other than the bronchi, particularly the skin, eyes and nasal mucosa and include such diseases as allergic rhinitis and urticaria.

Acute asthmatic bronchospasm has been treated with drugs which relax bronchial smooth muscle. Sympathomimetic drugs such as epinephrine, isoproterenol, and terbutaline and xanthine drugs such as theophylline and its salts (aminophylline, etc.) have been used for this purpose. Drugs such as cromolyn sodium which inhibit the release of allergic mediators, have been used prophylactically to treat bronchial asthma. Corticosteriod drugs have also been used to treat bronchial asthma and other allergy diseases.

Many of the drugs used hitherto have shortcomings which make them less than ideal for treatment of asthma and other bronchospastic and allergic diseases. For example, epinephrine and isoproterenol relieve the symptoms of asthma for only a relatively short period of time and are ineffective orally. Theophylline has limited efficacy and produces cardiac and gastrointestinal side effects. Cromolyn sodium is only effective by inhalation or injection and is ineffective by oral administration. The corticosteriod drugs have serious side effects which limit their chronic use.

Substituted xanthines have been known for some time as bronchodilators, and theophylline (1,3-dimethylxanthine) has long been used in the treatment of bronchial asthma.

Prior attempts have been made to improve theophylline by substituting the xanthine nucleus with different groups in several positions in the molecule. A number of 1,3-dialkylxanthines and 1,3,8-trialkylxanthines have been shown to be bronchodilators in animal models. However, none of the substituted xanthine compounds hitherto synthesized have displaced theophylline and its salts as clinically useful bronochodilator and antiallergy agents.

Stoll (Stoll, J. H. et.al., U.S. Pat. No. 2,729,643, issued Jan. 3, 1956.) describes the formation of intermediate products which he defines by way of a generic structural formula. This formula appears to broadly cover the compounds of this invention but Stoll has no specific disclosure of 3-(2-methyl-1-butyl) substituted xanthines.

Stoll's specific compounds of the 1,3,8-trialkylxanthine type are limited to those which have the same alkyl groups in both 1- and 3- position. He does not disclose any 1,3,8-trialkylxanthines having a 1-methyl group combined with a group in the 3-position having 4 to 7 carbon atoms.

Certain compounds disclosed by LeRoy, et.al., *J. Pharmacol. Exptl. Therap.* 69, 45–51 (1940), Speer, et.al., *J. Am. Chem. Soc.* 75, 114–115 (1953), and Stoll may be construed as being structurally similar to the compounds of this invention but none of these references suggests a bronchodilating or anti-allergen use.

Armitage, (Armitage, A. K., et.al., *Brit. J. Pharmacol.*, 17, 196–207 (1961).), who deals with certain di- and tri-alkyl xanthines, alleges uses relating to bronchodilation, but does not show a 2-methyl-1-butyl grouping in the 3-position. Thus, while a similar use is involved, the compounds of this invention and their improved properties are not suggested by these prior art compounds.

Goodsell, (Goodsell, E. B., et.al., *J. Med. Chem.* 1971, 14 (12) 1202–1205.) who deals with tri-alkyl xanthines, discusses the 3′, 5′-cyclic adenosine monophosphate phosphodiesterase inhibition by certain 1,3-dimethyl-8-alkylxanthines and also reports some pharmacological data for these compounds. However, Goodsell did not test these compounds for bronchodilation or antiallergy properties either in vitro or in vivo. Furthermore, no experiments were done to test the duration of activity of these compounds. Hence, Goodsell teaches nothing regarding the long-acting bronchodilation and antiallergy properties of 8-alkylxanthines.

Beavo (Beavo, J. A., et.al., *Mol. Pharmacol.* 6, 597–603) in a study of adenonine-3′, 5′-monophosphate phosphodiesterase activity of substituted xanthines discloses a few compounds having an 8-alkyl group. His in vitro data do not teach anything about duration of pharmacological activity in vivo.

A class of substituted xanthine compounds has now been found which are very effective bronchodilator and antiallergy agents with rapid onset and prolonged duration of action. These compounds are effective, rapid-acting bronchodilators by all routes of administration and accordingly can be used to abort an acute bronchospastic attack. In addition, they are orally effective, long-acting antiallergy compounds, by suppressing the release of allergic mediators. Hence, these compounds may be used prophylactically to treat bronchial asthma, and other bronchospastic and allergic diseases.

SUMMARY OF THE INVENTION

It is an object of this invention to provide a method of treating bronchial asthma and other bronchospastic and allergic diseases. A further object is to provide a method for treating bronchial asthma and other bronchospastic and allergic conditions by administering drugs comprising substituted xanthines. A further object is to provide a method of treatment which may be used prophylactically as well as in acute bronchospastic and allergic attacks. A further object is to provide a method for producing long-lasting relief of bronchial asthma and other bronchospastic and allergic diseases. A further object is to provide novel compounds for the treatment of bronchial asthma and other bronchospastic and allergic diseases.

According to this invention prolonged bronchodilation and prolonged inhibition of allergic mediator release in mammals are produced by administering an effective amount of a substituted xanthine compound having the formula:

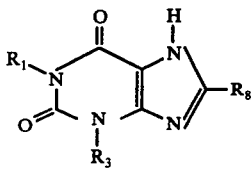

wherein:
$R_1$ = methyl
$R_3$ = $C_4$-$C_7$ alkyl, $C_4$-$C_7$ alkenyl, $C_4$-$C_7$ alkynyl, $C_4$-$C_7$ cycloalkyl or $C_4$-$C_7$ cycloalkylalkyl,
$R_8$ = $C_1$-$C_2$ alkyl Because of their pharmacological activity these compounds are useful in the treatment of bronchial asthma and other bronchospastic and allergic diseases.

These compounds may be administered orally, sublingually, parenterally, rectally or by inhalation in the form of tablets, capsules, solutions, suspensions, suppositories, aerosols and the like. Typical effective doses in humans range from 0.01 to 50 milligrams per kilogram of body weight, depending upon route of administration and potency of compound selected.

DESCRIPTION OF PREFERRED EMBODIMENTS

Suitable groups for $R_3$ in the compounds of this invention include n-butyl, i-butyl, 1-methyl-1-propyl, n-pentyl, 1-methyl-1-butyl, 2-methyl-1-butyl, 3-methyl-1-butyl, 2,2-dimethyl-1-propyl, n-hexyl, 1-methyl-1-pentyl, 2-methyl-1-pentyl, 3-methyl-1-pentyl, 4-methyl-1-pentyl, 2,2-dimethyl-1-butyl, 2,3-dimethyl-1-butyl, 3,3-dimethyl-1-butyl, 1-ethyl-1-butyl, 2-ethyl-1-butyl, n-heptyl, 1-methyl-1-hexyl, 2-methyl-1-hexyl, 3-methyl-1-hexyl, 4-methyl-1-hexyl, 5-methyl-1-hexyl, 1,2-dimethyl-1-pentyl, 2,2-dimethyl-1-pentyl, 2,3-dimethyl-1-pentyl, 1,3-dimethyl-1-pentyl, 2,4-dimethyl-1-pentyl, 1-ethyl-1-pentyl, 2-ethyl-1-pentyl, 2-ethyl-3-methyl-1-pentyl, cyclobutyl, cyclopentyl, cyclohexyl, methallyl, 2-methyl-2-buten-1-yl, 2-methyl-3-buten-1-yl, 3-methyl-2-buten-1-yl, 2-methyl-3-butyn-1-yl, cyclopropylmethyl, cyclobutylmethyl, cyclopentylmethyl, cyclohexylmethyl and 2-cyclopropylethyl and the like.

Suitable groups for $R_8$ include methyl and ethyl.

It is preferred to have $R_8$ = methyl. The introduction of an alkyl group in the 8-position of the xanthine nucleus has been discovered to produce a compound having a long lasting activity. As shown below in Example 3, the 8-alkylxanthine bronchodilators have a longer duration of activity than the corresponding 8-H xanthine. It is believed that the 8-alkyl group prevents the normal enzymic oxidation at the 8-position of xanthines and thereby prevents rapid bioinactivation of the xanthine.

It is preferred to have $R_3$ selected from the group consisting of n-butyl, isobutyl, n-pentyl, 2-methyl-1-butyl, 3-methyl-1-butyl, 2,2-dimethyl-1-propyl, n-hexyl, 2-methyl-1-pentyl, 3-methyl-1-pentyl, 4-methyl-1-pentyl, 2-methyl-1-hexyl, methallyl, cyclopropylmethyl, cyclobutylmethyl, and 2-cyclopropylethyl groups. More preferred $R_3$ groups are isobutyl, 2-methyl-1-butyl, 2-methyl-1-pentyl, 3-methyl-1-butyl, n-pentyl, 2,2-dimethyl-1-propyl, methallyl, cyclopropylmethyl and cyclobutylmethyl groups. Of these the isobutyl and 2-methyl-1-butyl are most preferred and 2-methyl-1-butyl is uniquely preferred. This group has never been reported as a substituent in a xanthine compound and has a significant advantage over the prior art $R_3$ groups.

In comparison with the known $R_3$ groups, as shown below in Example 4, the 2-methyl-1-butyl group surprisingly confers on the xanthine bronchodilators an effectiveness equal to the best $R_3$ group reported in the prior art, the isobutyl group. This is surprising because the next higher homolog, the 2-methyl-1-pentyl group, confers much lower bronchodilation potency. Furthermore, the 2-methyl-1-butyl surprisingly combines this great potency with a substantially lower toxicity. Thus the 2-methyl-1-butyl group is uniquely suitable for the $R_3$ group of a xanthine bronchodilator and such compounds which contain it are greatly preferred.

A highly preferred compound is 1,8-dimethyl-3-isobutylxanthine, This compound has great potency and is long-acting. The most preferred compound is that which combines the preferred groups, namely 1,8-dimethyl-3-(2-methyl-1-butyl)xanthine.

This compound has a unique combination of high potency, relatively low toxicity, and long-lasting activity.

The 1,3,8-trialkylxanthines can be prepared by the well-known general procedure of Traube, Berichte 33, 1371 and 3055 (1900).

A 1,3-dialkyl urea having the general formula

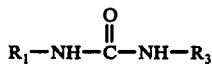

is first prepared. This urea can be prepared by reacting one mole of an alkyl isocyanate with one mole of an amine according to the reaction

It is evident from the symmetry of the product that either $R_1$ or $R_3$ may be in the isocyanate reagent and either group may be in the amine reagent. The conditions under which this well-known reaction proceeds are known to one skilled in the art.

The isocyanate required for the above reaction may be prepared by reacting the corresponding amine with phosgene according to the equation.

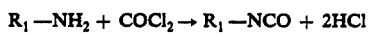

The conditions for this reaction are well known to those skilled in the art and are described in the chemical literature, e.g., in British patent specification No. 901,337.

The 1,3-dialkyl urea is next converted into a 1,3-dialkyl-1-cyanoacetylurea by reaction with cyanoacetic acid according to the following reaction:

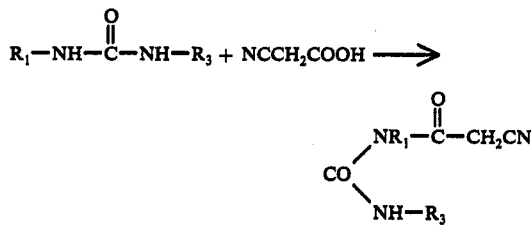

The reaction is conveniently carried out in acetic anhydride at 60° to 70°. The reaction gives preferentially although not exclusively the product containing the smaller alkyl group as $R_1$. The isomers may be separated by fractional crystallization. The 1,3-dialkyl-1-cyanoacetylurea is next cyclized to form a 4-amino-1,3-dialkyluracil according to the following reaction:

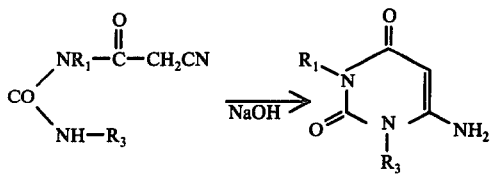

The reaction is carried out by treating the 1,3-dialkyl-1-cyanoacetylurea with a strong base such as sodium hydroxide in an aqueous medium.

The 4-amino-1,3-dialkyl uracil is then converted into 4-amino-5-nitroso-1,3-dialkyluracil by treating with sodium nitrite in glacial acetic acid at room temperature, according to the following reaction:

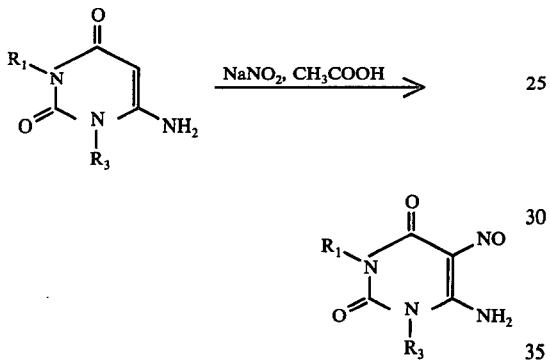

The 4-amino-5-nitroso-1,3-dialkyl-uracil is then reduced to a 4,5-diamino=1,3-dialkyluracil by reaction with sodium dithionite in ammonium hydroxide solution according to the following reaction:

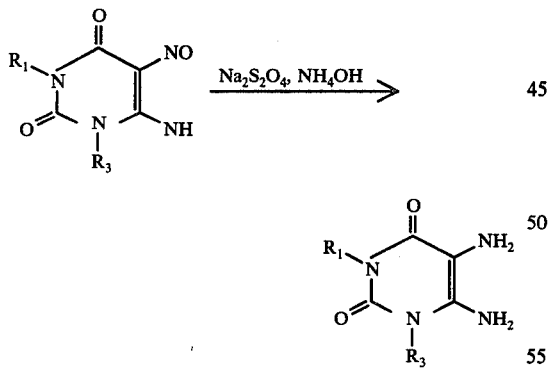

The 4,5-diamino-1,3-dialkyluracil is next converted to a 4-amino-5-alkylamino-1,3-dialkyluracil by reacting with a lower aliphatic acid according to the following equation:

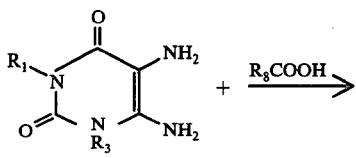

-continued

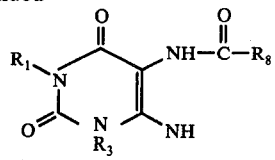

wherein $R_8$ is a lower group.

The 4-amino-5-alkanoylamino-1,3-dialkyluracil is then cyclized to form the 1,3,8-trialkylxanthine by heating in 10% aqueous sodium hydroxide solution to reflux temperature according to the following equation.

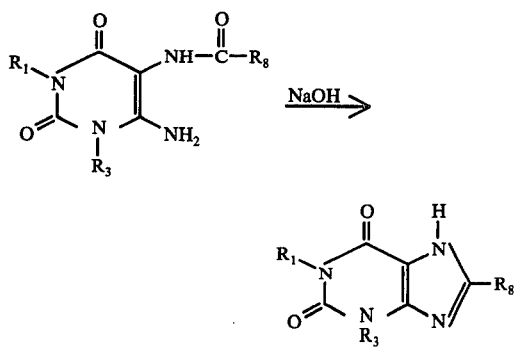

The compounds of this invention wherein $R_3$ contains an asymmetric carbon atom can exist in optically active enantiomeric forms. These forms may exist separately or mixed in any proportions. The racemic, or equimolar mixture of enantiomeric forms is obtained in the synthesis using reagents devoid of optical activity. The optically active forms of the substituted xanthines can be prepared by using the corresponding optically active amines $R_3NH_2$ in the synthesis. For example, the optically active dextro- or levo- form of the substituted xanthines having $R_3 = CH_2CH(CH_3)CH_2 CH_3$ can be obtained by starting with the corresponding optically active form of 2-methylbutylamine. Dextro- and levo-2-methylbutylamines can be prepared by from the corresponding commericially available dextro- and levo-2-methylbutanols by the procedure described by Vasi, I. G., and Desai, R. K., *J. Inst. Chemists Calcutta*, 45, 66 (1973).

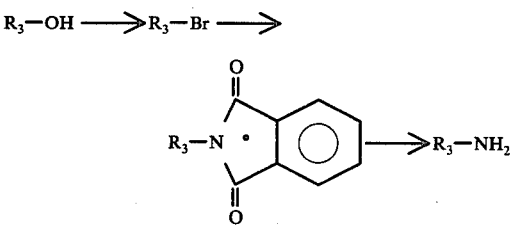

The compounds of this invention may be administered in the customary ways such as orally, sublingually, inhalation, rectally, and parenterally. Tablets, capsules, solutions, suspensions and aerosol mist may be used as forms for administration.

The compounds of this invention can be formulated into compressed tablets incorporating the customary excipients including diluents, binders, lubricants, disintegrants, colors, flavors, and sweetening agents. Commonly used pharmaceutical diluents such as calcium sulfate, lactose, kaolin, mannitol, sodium chloride, dry starch, and powdered sugar may be used.

Suitable binders for tablets include starch, gelatin, sugars, such as sucrose, glucose, lactose, molasses, natural and synthetic gums such as acacia, sodium alginate, extract of Irish moss, panwar gum, ghatti gum, carboxymethyl cellulose, polyvinylpyrrolidone and the like.

Commonly used lubricants which are suitable for tablets include talc, magnesium stearate, stearic acid, hydrogenated vegetable oils, and the like.

A suitable disintegrant may be incorporated into the tablets. Suitable disintegrants such as starches, clays cellulose, algins, and gums may be used as is well known to those skilled in the art.

Conventional coloring agents such as pharmaceutically acceptable dyes and lakes and flavoring agents such as mannitol, lactose, or artificial sweetners may also be added to the tablet composition.

The compounds of this invention may also be administered orally contained in hard or soft capsules of gelatin or other suitable material. The compound of this invention may be present in the capsule alone or mixed with a suitable diluent such as lactose or starch.

The compounds of this invention may also be administered sublingually as rapidly disintegrating tablets or as troches or sublingual lozenges or pastilles. These dosage forms are prepared by mixing the active ingredient with flavored, rapidly dissolving or rapidly disintegrating excipients. For example a suitable base would comprise starch, lactose, sodium saccharin and talc.

Parenteral means can also be used for administering the compounds of this invention. They may be incorporated into implantable, slow-dissolving pellets or into aqueous injectable suspensions or solutions, or oily injectable media such as fixed oils.

The compounds of this invention may also be administered by inhalation of a mist. The active compound may be dissolved or suspended in an aerosol propellant or suitable carrier liquid and loaded into a standard aerosol container with sufficient propellant to provide the proper pressure for dispensing the compound. These propellants are usually fluorinated or fluorochlorinated lower saturated alphatic hydrocarbons. The active ingredient is then dispensed through a special valve in the form of a fine mist which is inhaled.

The great potency of 1,8-dimethyl-3-(2-methyl-1-butyl) xanthine makes it a preferred compound for aerosol administration, like epinephrine and isoproterenol, to abort acute attacks. Aerosols of theophylline and its salts have been tried in the art, but the high doses required for these drugs to be efficacious makes this mode of administration impractical.

It is preferred to administer the bronchodilator and antiallergy compounds of this invention orally in the form of tablets or capsules. Preferred oral dosage range in humans is from 2 to 50 mg. twice daily.

The following examples illustrate the practice of this invention buty are not intended to limit its scope.

EXAMPLE 1

Synthesis of 1,8-dimethyl-3-(2-methyl-1-butyl) xanthine

Step 1

1-methyl-3-(2-methyl-1-butyl) urea (1)

1.03 kg (11.8 mole) of 2-methyl-1-butylamine was added to 4.5 L of chloroform and the solution cooled to 0°–5° C.

Then 674.0 g (11.8 mole) of methyl isocyanate was added slowly while maintaining the temperature at 0.5° C.

After the addition was complete the reaction was allowed to reach room temperature. Stirring was continued for 18 hrs.

The chloroform was removed under vacuum to yield ~ 1.7 kg of 1-methyl-3-(2-methyl-1-butyl) urea (1) — an oil. Yield 100%.

Step 2

1-methyl-1-cyanoacetyl-3-(2-methyl-1-butyl) urea (2)

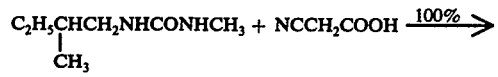

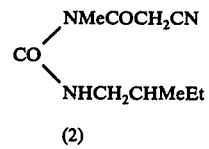

To ~ 1.7 kg (11.8 mole) of 1-methyl-3-(2-methyl-1-butyl)urea (1) were added 4.3 L of acetic anyhydride and 1.18 kg (13.9 mole) of cyanoacetic acid. This was heated for 2 hr. at 60°–70° C.

The acetic anhydride was removed under vacuum to yield ~ 2.9 kg of an oil. This material is a mixture of cyano acetic acid and 1-methyl-1-cyanoacetyl-3-(2-methyl-1-butyl)urea (2) No attempt was made at purification; (2) was used immediately in the next step.

Step 3

4-amino-1-methyl-3-(2-methyl-1-butyl) uracil (3)

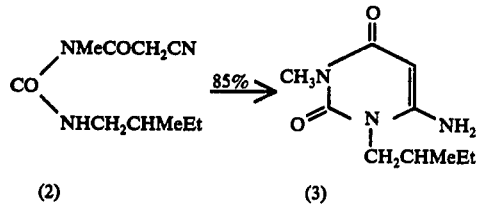

10.3 of 10% NaOH solution was slowly added to 2.9 kg (11.8 mole) of crude 1-methyl-1-cyanoacetyl-3-(2-methyl-1-butyl) urea (2) with stirring.

The oil dissolved and shortly another oil precipitated. The temperature rose to ~ 60° C and then dropped.

After stirring for awhile at room temperature the oil crystallized.

After cooling the product was filtered. The crude product was slurried in water and dried at 50° C in vacuo to yield ~ 2.1 kg of 4amino-1-methyl-3-(2-methyl-1-butyl) uracil (3) (m.p. 121° -124° C). Yield 85% from (1).

Step 4

4-amino-5-nitroso-1-methyl-3-(2-methyl-1-methyl-1-butyl) uracil (4)

[Reaction scheme: (3) → (4), 80%]

21. kg (9.9 mole) of 4-amino-1-methyl-3(2-methyl-1-butyl)-uracil (3) was suspended in 22.0 L of water. A solution of 745.5 L g (10.8 mole) of sodium nitrite in 5.7 L of water was added to the suspension. Then 1.2 L of glacial acetic acid was added dropwise and the suspension was stirred for 18 hr. at room temperature.

After cooling the precipitate was filtered. The crude product was slurried in water and dried at 80° C in vacuo to yield ~ 1.9 kg of 4-amino-5-nitroso-1-methyl-3-(2-methyl-1-butyl)-uracil (4) (m.p. 202°-204° C). Yield 80%.

Step 5

4,5-diamino-1-methyl-3-(2-methyl-1-butyl) uracil (5)

[Reaction scheme: (4) → (5), 70%]

8.65 L of conc. ammonium hydroxide (58%) was added to 1.9 kg (7.9 mole) of 4-amino-5-nitroso-1-methyl-3-(2-methyl-1-butyl)uracil (4). An orange salt formed.

The suspension was placed in an oil bath at 80°-90° C and a solution resulted.

5.6 kg (32.3 mole) of sodium dithionite was added in portions over about 30 min. When the addition was complete stirring was continued for 30 min.

The reaction was allowed to cool to room temperature and stirred overnight.

After cooling the precipitate was filtered, slurried with water and dried at 80° C in vacuo to yield ~ 1.25 kg of 4,5-diamino-1-methyl-3-(2-methyl-1-butyl)uracil (5) (m.p. 161°-163° C). Yield 70%.

Step 6

4-amino-5acetylamino-1-methyl-3-(2-methyl-1butyl)uracil (6)

[Reaction scheme: (5) → (6), 85%]

1.25 kg (5.5 mole) of 4,5-diamino-1-methyl-3-(2-methyl-1-butyl)uracil (5) was added to 4.5 L of glacial acetic acid and heated to reflux for 2 hrs.

The acetic acid was evaporated and the residue triturated with ether. The solid was filtered and dried at 60° C in vacuo to yield ~ 1.26 kg of 4-amino-5-acetylamino-1-methyl-3-(2-methyl-1-butyl)uracil (6) (m.p. 178°-182° C). Yield 85%.

Step 7

1,8-dimethyl-3-(2-methyl-1-butyl) xanthine (7)

[Reaction scheme: (6) → (7), 85%]

1.26 kg (4.7 mole) of 4-amino-5acetylamino-1-methyl-3-(2-methyl-1-butyl)uracil (6) was added to 3.9 L of 10% sodium hydroxide solution and heated at reflux for 30 min.

The solution was filtered and the filtrate cooled to room temperature.

The pH of the filtrate was adjusted to 5.0 with glacial acetic acid.

After cooling the precipitate was filtered. The crude product was slurried twice with water and dried at 80° C in vacuo to yield about 1.0 kg of 1,8-dimethyl-3-(2-methyl-1-butyl)xanthine (7) (m.p. 189°-191° C). Yield 85%.

EXAMPLE 2

1,3,8-Trialkylxanthines

By the procedure of Example 1 of a number of 1,3,8-trialkylxanthines are synthesized. By proper choice of the reagents containing the precursors of the $R_1$, $R_3$ and $R_8$ groups the particular compounds are synthesized. $R_1$ and $R_3$ are determined by the carboxylic acid reagent used in Step 5. Table 1 shows the reagents used in Steps 1 and 5 to introduce $R_1$, $R_3$ and $R_8$ and produce the listed compound.

TABLE 1

| No. | Compound | STEP 1 isocyanate | STEP 1 amine | STEP 5 acid |
|---|---|---|---|---|
| 4525 | 1,8-dimethyl-3-(n-butyl)xanthine | methyl isocyanate | n-butylamine | acetic acid |
| 4388 | 1,8-dimethyl-3-isobutylxanthine | methyl isocyanate | isobutylamine | acetic acid |
| 4506 | 1,8-dimethyl-3-n-pentylxanthine | methyl isocyanate | pentylamine | acetic acid |
| 4500 | 1,8-dimethyl-3-isopentylxanthine | methyl isocyanate | isopentylamine | acetic acid |
| 6738 | 1,8-dimethyl-3-(2,2-dimethylpropyl)-xanthine | methyl isocyanate | neopentylamine | acetic acid |
| 6842 | 1,8-dimethyl-3-n-hexyl)xanthine | methyl isocyanate | n-hexylamine | acetic acid |
| 4515 | 1,8-dimethyl-3-(2-methyl-1-pentyl)-xanthine | methyl isocyanate | 2-methyl-1-pentyl amine | acetic acid |
| 6786 | 1,8-dimethyl-3-(2-methyl-1-hexyl)-xanthine | methyl isocyanate | 2-methyl-1-hexyl-amine | acetic acid |
| 6794 | 1,8-dimethyl-3-methallylxanthine | methyl isocyanate | methallylamine | acetic acid |
| 6788 | 1,8-dimethyl-3-cyclohexylxanthine | methyl isocyanate | cyclohexylamine | acetic acid |
| 4530 | 1,8-dimethyl-3-cyclohexylmethylxanthine | methyl isocyanate | cyclohexanemethyl-amine | acetic acid |
| 6822 | 1,8-dimethyl-3-cyclopropylethylxanthine | methyl isocyanate | 2-cyclopropylethyl-amine | acetic acid |
| 6807 | L-1,8-dimethyl-3-(2)-methyl-1-butyl)xanthine | methyl isocyanate | L-2-methyl-1-butyl amine | acetic acid |
| 6796 | D-1,8-dimethyl-3-(2-methyl-1-butyl)xanthine | methyl isocyanate | D-2-methyl-1-butyl amine | acetic acid |
| 4490 | DL-1-methyl-3-(2-methyl-1-butyl)-8-ethyl-xanthine | methyl isocyanate | 2-methyl-1-butyl-amine | propionic acid |
| 6973 | 1,8-dimethyl-3-cyclopropylmethyl-xanthine | methyl isocyanate | cyclopropylmethyl-amine | acetic acid |
| 6982 | 1,8-dimethyl-3-cyclobutylmethylxanthine | methyl isocyanate | cyclobutylmethyl-amine | acetic acid |

In the following comparative examples results of pharmacological tests with a number of the compounds of this invention and of the prior art are presented. The pharmacological properties were evaluated by standard tests which are defined, together with the symbols used as follows:

BD: Bronchodilator activity evaluated against histamine-induced bronchoconstriction in the guinea pig, and expressed as % protection at the stated time interval (in minutes and hours) post-drug against histamine agonist. Doses are expressed in milligrams per kilogram of body weight (mpk) per os (po) or intraperitoneally (ip).

A modification of the method of Siegmund. O. H., et.al., J. Pharmacol. and Exp. Therap. 90:254–9, 1947, is used. Healthy guinea pigs weighing from 250 to 300 grams are placed four at a time and separated by wiring screening in an 11 liter plastic chamber, at the time of peak activity following drug administration. The challenge consists of histamine diphosphate (1% solution) aerosolized in a de Vilbiss #40 nebulizer at 200 mm Hg. Times for prostration are recorded. All animals exposed to the aerosols for 10 minutes or longer without prostration, are arbitrarily considered fully protected.

Per cent protection is calculated as follows:

$$\% \text{ Protection} = \frac{100(\text{Test prostration time} - \text{control prostration time})}{600 - \text{control prostration time}}$$

wherein the times are measured in seconds.

CP: Cardiopulmonary activity evaluated against histamine-induced bronchoconstriction in the dog and expressed as % increase ($\uparrow$) or decrease ($\downarrow$) in the following parameters:
BP: blood pressure
HR: heart rate
PR: pulmonary resistance
PC: pulmonary compliance
RMV: respiratory minute volume The method used is that of Giles, R. E., Finkel, N. P., and Mazurowski, J., Arch. Int. Pharmacodyn. Therap. 194, 213 (1971). A simulated asthmatic state is induced in anesthetized spontaneously breathing dogs by graded intravenous doses of histamine. The degree of induced bronchoconstriction is reflected by proportionate increases in pulmonary resistance. Pretreatment with bronchodilator drugs aims to block the bronchospastic response to histamine. Each dog serves as its own control. Mean values 2 hours post drug are given.

SP: Spasmolytic activity evaluated in vitro using guinea pig tracheal chain preparation, and expressed as the molar (M) concentration required to produce maximum relaxation.

The method used in that of Castillo and de Beer, J. Pharmac. Expt. Therap. 90, 104, 1947.

AA: Antiallergy (anti-anaphylactic) activity evaluated against antigen-induced bronchconstriction in rats sensitized with N. brasliensis, and expressed as % protection (R).

The method used in that of Church, N. K. Collier, H. O. J., and James, G. W. L., Brit. J. Pharmacol. 46, 56–65 (1972). Rats sensitized with antigen from Nippostrongylus brasiliensis exhibit anaphylactic shock when reexposed to this antigen 28 days later. The animals are subdivided into control and test groups.

Test animals receive a drug either orally, intraperitoneally or intravenously and are challenged with intravenous antigen at fixed time intervals after dosing. Antigen-induced increases in tracheal pressure are monitored and reflect the extent of bronchoconstriction.

PCA: Antianaphylactic activity against passive cutaneous anaphylaxis in the rat, expressed as % protection against antigen-induced wheal formation.

The method used is that of Ogilvie, B. M., *Immunology* 12, 113–131 (1967). Reaginic AgE antibodies develope in that rat following subcutaneous injection of Nippostrongylus brasiliensis larvae. Antisera, collected 28 days later are injected subcutaneously into new rats. These new rats when challenged with antigen 24 hours later exhibit and immediate type I reaction characterized by local swelling and edema (wheal) at the site of antisera injection.

compound. The unexpectedly prolonged activity of the 1,3,8-trialkylxanthines may be seen in Table 2 which compares the activity of corresponding pairs of substituted xanthines with and without 8-alkyl groups. The data on bronchodilator activity in the guinea pig (BD[guinea pig]) shows the prolonged activity of the compounds having an 8-alkyl group. In each pair the protection at 4 hours or 6 hours produced by the corresponding compound devoid of the 8-methyl group. Data at equal doses and the same time is shown for the pairs 4383 vs. 4280, 4388 vs. 4258 and 4296 vs. theophylline.

TABLE 2

PROLONGED ACTIVITY OF 8-ALKYLXANTHINES

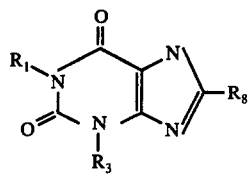

| Cpd. | $R_1$ | $R_3$ | $R_8$ | $R_7$ | BD (guinea pig) | | | | | | AA (rat) | | SP in vitro C | $LD_{50}$ | |
|---|---|---|---|---|---|---|---|---|---|---|---|---|---|---|---|
| | | | | | mpK | 30' | 1h | 2h | 4h | 6h | 8h | mpK | 1h | | mpK | spec. |
| 4280 | $CH_3$ | $CH_2CHMeEt$ | H | H | 20po 80po | 86 lethal | 86 | 80 3/8 | 13 | | | 15ip | 56 | M/1000 | | |
| 4383 | $CH_3$ | $CH_2CHMeEt$ | $CH_3$ | H | 10po 20po | 35 | 63 92 | | 100 | 66 97 | | 2½ po 4ip | 58 57 | M/1000 | 21.7po 24.6ip 88.7po 66.6po | g. pig rat rat mouse |
| 4258 | $CH_3$ | $CH_2CHMe_2$ | H | H | 15po 25po | 45 lethal | 75 2/4 | | 39 | | | 1.5ip 2.0ip | 79 tox | M/1000 | | |
| 4388 | $CH_3$ | $CH_2CHMe_2$ | $CH_3$ | H | 10po 20po | lethal | 76 1/4 | | 73 | 80 | | 2.5po | 50 | M/1000 | | |
| Theophylline | $CH_3$ | $CH_3$ | H | H | 80po 100po | 32 45 | 69 58 | 42 36 | 17 25 | 14 | | 75ip 225po 100po | 70 50 73 | M/10 | 183po 225po 150ip | g. pig rat rat |
| 4296 | $CH_3$ | $CH_3$ | $CH_3$ | H | 100po 150po | 68 | 53 80 | 71 | 45 79 | 43 86 | 23 85 | 75ip | 49 | M/14 | | |

$LD_{50}$: Dose required to cause death of 50% of test animals.

The $LD_{50}$ was determined in three species, the mouse (male, 18–25 g), the albino rat (female, 150–200 g) and the albino guinea pig (male 180–280 g) by oral administration and in the albino rat by intraperitoneal administration. The animals are fasted overnight prior to testing. Six groups of 10 animals are used; five groups are dosed with the test substance, the sixth group serves as a control and receives the drug vehicle at the highest test concentration. The compounds were administered in a 0.5% gum tragacanth solution in distilled water using a constant logarithmic increment in dose. Dose volume ranged from 5 to 40 mg/kg.

The animals were housed five per cage (rat and guinea pig) or ten per cage (mouse) with free access to food and water. The number of dead animals was recorded daily for five consecutive days. The total mortality per group of 10 for each dose level was recorded and and $LD_{50}$ with Confidence Limits calculated according to the method described by Weil, C. S., *Biometrics* 8(3): 249–263, 1952.

EXAMPLE 3

This example illustrates the prolonged activity of the 8-alkylxanthine over that of the corresponding 8-H

EXAMPLE 4

This example illustrates the decreased toxicity of substituted xanthines having $R_3$ = 2-methyl-1-butyl over those having $R_3$ = isobutyl while the potency of the compounds remains approximately equal.

The unexpected improvement in activity of 1-alkyl-3-(2-methyl-1-butyl)xanthines, without a corresponding increase in toxicity with reference to the corresponding 3-isobutyl homologs can be seen in Table 3 where the data for corresponding pairs of compounds are presented. 4383 has about the same bronchodilation potency as 4388 in the BD (guinea pig) assay at a dose of 10 mpK per os; yet at a dose of 20 mpK po 4383 shows no toxic effects while 4388 shows pronounced toxicity and was even lethal to one animal.

4280 and 4258 show equal potency as shown by the results for doses of 20 mpK po and 15 mpK po respectively; however 4258 shows lethal effects at only 25 mpK po while 4280 must be given at a dose of 80 mpK po to show similar lethal effects.

Clearly, the xanthines having a 2-methyl-1-butyl group in the 3-position are less toxic than those having a 3-isobutyl group.

TABLE 3
EQUAL ACTIVITY WITHOUT INCREASE TOXICITY 3-(2-METHYLBUTYL VS. 3-ISOBUTYL)

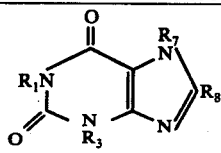

| | $R_1$ | $R_3$ | $R_8$ | $R_7$ | BD (guinea pigs) mpK | 30' | 1h | 2h | 4h | 6h | 8h | AA (rat) mpK | 11h | SP in vitro C | $LD_{50}$ mpK spec. |
|---|---|---|---|---|---|---|---|---|---|---|---|---|---|---|---|
| 4388 | $CH_3$ | $CH_2CHMe_2$ | $CH_3$ | H | 10po 20po | lethal | 76 | 1/4 | 73 | 80 | | 2.5po | 50 | M/1000 | |
| 4383 | $CH_3$ | $CH_2CHMeEt$ | $CH_3$ | H | 10po 20po | 35 | 63 92 | | 100 | 66 97 | | 2.5po | 58 | M/1000 | 21.7po g. pig 24.6ip rat 88.7po rat 66.6po mouse |
| 4258 | $CH_3$ | $CH_2CHMe_2$ | H | H | 15po 25po | 45 lethal | 75 | 2/4 | 39 | | | 1.5ip 2.0ip | 79 tox | M/1000 | |
| 4280 | $CH_3$ | $CH_2CHMeEt$ | H | H | 20po 80po | 86 lethal | 86 | 80 3/8 | 13 | | | 15ip | 56 | M/1000 | |

*Mean value

EXAMPLE 5

This example illustrates the activity of another compound of this invention.

Table 4 gives the results of testing 1,8-dimethyl-3-(2-methyl-1-pentyl)xanthine in the guinea pig bronchodilation, rat antiallergy, and in vitro bronchodilation potency tests.

TABLE 4
PHARMACOLOGICAL ACTIVITY OF 1,8-DIMETHYL-3-(2-METHYL-1-PENTYL) XANTHINE

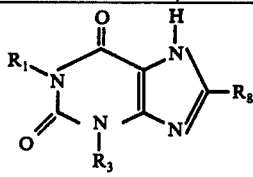

| Cpd. | $R_1$ | $R_3$ | $R_8$ | BD (guinea pig) mpK | 30' | 1h | 2h | 4h | 6h | 8h | AA (rat) mpK | 1h | SP in vitro C |
|---|---|---|---|---|---|---|---|---|---|---|---|---|---|
| 4373 | $CH_3$ | $CH_2CHMePr$ | $CH_3$ | 40po 80po | 71 81 | | | 87 100 | 96 | | 20ip | 54 | M/20 |

EXAMPLE 6

This example illustrates the antiallergy properties of the compounds of this invention.

1,8-Dimethyl-3-(2-methyl-1-butyl)xanthine was tested in the rat passive cutaneous anaphylaxis screen described above. The data in Table 6 shows that these compounds are effective in this assay which measures a purely anti-allergic activity.

The results of studies of cardiopulmonary activity in the dog by the above-described procedures are shown in Table 6. The data shows that compound 4383 significantly reduces the decrease in pulmonary compliance and increase in pulmonary resistance due to histamine administration. The corresponding values for theophylline, a clinically used xanthine bronchodilator, are shown for comparison. It can be seen that the compounds of this invention are more potent bronchodilators than theophylline in the dog.

TABLE 6
CARDIOPULMONARY ACTIVITY IN THE DOG

| | | CP (dog) (mean value at 2h) | | | | |
|---|---|---|---|---|---|---|
| | mpK | BP | HR | PC | PR | RMV |
| 4383 | 1po | ↓12 | ↑21 | ↑18 | ↓36 | ↑33 |
| Theophylline | 40po | ↓08 | ↑06 | ↑25 | ↓36 | ↑38 |

TABLE 5
PERCENT PROTECTION IN THE RAT PASSIVE CUTANEOUS ANAPHYLAXIS SCREEN

| No. | Compound | Dose (mg/kg) & Route | Wheal Diameter (cm): Mean ± S.E.M. Control | Response | % Δ | Wheal Intensity: Mean ± S.E.M. Control | Response | % Δ |
|---|---|---|---|---|---|---|---|---|
| 4383 | 1,8-dimethyl-3-(2-methyl-1-butyl)xanthine | 20po | 1.50 ± 0.16 | 0.74 ± 0.16 | 50. | 2.17 ± 0.21 | 1.13 ± 0.27 | 48 |

EXAMPLE 7

This example illustrates the pharmacological activity of the compounds of this invention in the dog.

EXAMPLE 8

Tablets 19.5 grams of starch are dried to a moisture content of 10%. 0.5 grams of 1,8-dimethyl-3-(2-methyl-1-butyl)xanthine in finely powdered form are thoroughly mixed with the starch. The mixture is compressed into slugs. The slugs are reground into powder of 14-16 mesh size. This powder is recompressed into tablets weighing 200 mg. each. Each tablet thus has the composition:

1,8-dimethyl-3-(2-methyl-1-butyl)-xanthine: 5 mg.
starch: 195 mg.

EXAMPLE 9

Capsules

A dry mixture of 19.5 grams of starch and 0.5 grams of 1,8-dimethyl-3-(2-methyl-1-butyl)xanthine is prepared as described in Example 8. The powder is loaded into hard gelatin capsules so that each capsule contains 200 mg. of the powder.

EXAMPLE 10

Sublingual Tablets

Tablets for sublingual administration were prepared by standard procedure, each tablet containing 5 mg. of 1,8-dimethyl-3-(2-methyl-1-butyl)xanthine in a rapidly disintegrating base comprising starch, lactose, sodium saccharin and talcum.

EXAMPLE 11

Aerosol

Five grams of 1,8-dimethyl-3-(2-methyl-1-butyl)xanthine were dissolved in 1000 grams of a mixture of 20 parts by weight of dichlorodifluoromethane and 80 parts by weight of 1,2-dichloro-1,1,2,2-tetrafluoroethane and loaded into a conventional aerosol medication dispenser to provide a means of administering the active ingredient by inhalation.

I claim:

1. A method for producing prolonged bronchodilation and prolonged inhibition of allergic mediator release in mammals by administering to a mammal in need thereof an effective amount of a compound having the formula:

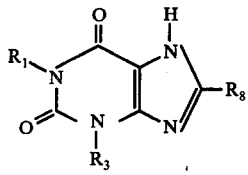

wherein:
$R_1$ = methyl
$R_3$ = $C_4$-$C_7$ alkyl, $C_4$-$C_7$ alkenyl, $C_4$-$C_7$ alkynyl, $C_4$-$C_7$ cycloalkyl, $C_4$-$C_7$ cycloalkylalkyl
$R_8$ = $C_1$-$C_2$ alkyl.

2. A method according to claim 1 wherein $R_3$ is —$CH_2(C_3$-$C_6$ alkyl).

3. A method according to claim 1 wherein $R_3$ is —$CH_2$—($C_3$-$C_6$ cycloalkyl).

4. A method according to claim 1 wherein $R_3$ is selected from the group consisting of methallyl, n-butyl, isobutyl, n-pentyl, 2-methyl-1-butyl, 3-methyl-1-butyl, 2,2-dimethylpropyl, 2-methyl-1-pentyl, cyclopropylmethyl, and cyclobutylmethyl.

5. A method according to claim 1 wherein $R_3$ is 2-methyl-1-butyl.

6. A method according to claim 1 wherein $R_3$ is isobutyl.

7. A method according to claim 1 wherein $R_8$ is ethyl.

8. A method according to claim 1 wherein $R_8$ is methyl.

9. A method according to claim 1 wherein said substituted xanthine is 1,8-dimethyl-3-(2-methyl-1-butyl)xanthine.

10. A method according to claim 1 wherein said substitued xanthine is 1,8-dimethyl-3-isobutylxanthine.

11. A method according to claim 1 wherein said substituted xanthine is administered to humans in a dose of between 0.2 and 200 mg.

12. A method according to claim 1 wherein said substituted xanthine is incorporated with inert excipients into a capsule and administered orally.

13. A method according to claim 1 wherein said substituted xanthine is incorporated with inert excipients into a tablet and administered orally.

14. A method according to claim 1 wherein said substituted xanthine is incorporated with inert excipients into a rapidly disintegrating tablet and administered sublingually.

15. A method according to claim 1 wherein said substituted xanthine is incorporated with propellant and solvent into an aerosol and administered by inhalation of the mist.

16. A method according to claim 1 wherein said substituted xanthine is incorporated with fatty vehicles into a suppository and administered rectally.

17. A method according to claim 1 wherein said substituted xanthine is incorporated with a sterilized vehicle and administered parenterally.

18. A compound having the formula:

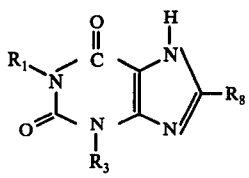

wherein:
$R_1$ = methyl
$R_3$ = $CH_2$—($C_3$-$C_4$ alkyl), —$CH_2$—($C_3$-$C_4$ cycloalkyl),
$R_8$ = $C_1$-$C_2$ alkyl.

19. A compound according to claim 18 wherein $R_3$ is selected from the group consisting of isobutyl and 2-methyl-1-butyl.

20. A compound according to claim 18 wherein $R_3$ is n-butyl.

21. A compound according to claim 18 wherein $R_3$ is isobutyl.

22. A compound according to claim 18 wherein $R_3$ is n-pentyl.

23. A compound according to claim 18 wherein $R_3$ is isopentyl.

24. A compound according to claim 18 wherein $R_3$ is 2-methyl-1-butyl.

25. A compound according to claim 18 wherein $R_3$ is cyclopropylmethyl

26. A compound according to claim 18 wherein $R_3$ is cyclobutylmethyl.

27. A compound according to claim 18 wherein $R_8$ is ethyl.

28. A compound according to claim 18 wherein $R_8$ is methyl.

29. 1,8-dimethyl-3-(2-methyl-1-butyl)xanthine.

30. dextro-1,8-dimethyl-3-(2-methyl-1-butyl)xanthine.

31. levo-1,8-dimethyl-3-(2-methyl-1-butyl)xanthine.

32. 1,8-dimethyl-3-isobutylxanthine.

33. A pharmaceutical composition comprising an amount of a compound according to claim 18 effective for bronchodilation in combination with a non-toxic inert pharmaceutically acceptable diluent.

34. A composition according to claim 33 in the form of a tablet.

35. A composition according to claim 33 in the form of a capsule.

36. A composition according to claim 33 in the form of a sublingual tablet.

37. A composition according to claim 33 wherein said diluent is an aerosol propellent.

38. A composition according to claim 33 comprising 1,8-dimethyl-3-(2-methyl-1-butyl)xanthine dissolved in a pharmaceutically acceptable aerosol propellant.

39. A pharmaceutical composition in the form of a tablet comprising between 1 mg and 100 mg of a compound according to claim 18 in combination with non-toxic pharmaceutically acceptable excipients.

* * * * *

UNITED STATES PATENT OFFICE
CERTIFICATE OF CORRECTION

Patent No. 4,089,959                     Dated May 16, 1978

Inventor(s) Julius Diamond

It is certified that error appears in the above-identified patent and that said Letters Patent are hereby corrected as shown below:

Column 2, line 25, "antillergy" should read --antiallergy--; Column 8, line 62, insert "L" after "10.3"; Column 9, line 4, insert "-" after "∿2.1 kg of 4"; Column 9, line 10, delete "methyl-1-" at the end of the line; Column 9, line 25, delete "L" after "745.5"; Column 10, line 3, insert "-" after "...amino-5"; Column 10, line 3, insert "-" after "...(2-methyl-1"; Column 10, line 44, insert "-" after "...amino-5"; Column 10, line 61, delete "of" after "...of Example 1"; Table 1, Column 1, compound #13 delete ")" after "...dimethyl-3-(2"; Column 13, line 10, "and" should read --an--; Column 14, line 61, insert "about" after "...4258 show"; Table 4, "1h" section, the numbers "71" and "81" should be directly under the column heading "1h".

Signed and Sealed this

Thirty-first Day of October 1978

[SEAL]

Attest:

RUTH C. MASON
Attesting Officer

DONALD W. BANNER
Commissioner of Patents and Trademarks